United States Patent
Tseng

[11] Patent Number: 5,626,270
[45] Date of Patent: May 6, 1997

[54] DRIP SYRINGE NEW BACKPACK FRAME

[75] Inventor: Chun-Long Tseng, Taipei, Taiwan

[73] Assignee: Chyi Shing Plastic Factory Co., Ltd., Taipei, Taiwan

[21] Appl. No.: 530,420

[22] Filed: Sep. 19, 1995

[51] Int. Cl.$^6$ .............................. A45F 3/10; A45F 5/00; A61M 5/14
[52] U.S. Cl. .................... 224/148.7; 224/148.2; 224/190; 224/628; 224/640; 224/262; 224/907; 128/DIG. 6
[58] Field of Search .......................... 224/148.2, 148.7, 224/189, 190, 628, 261, 262, 907, 640; 128/DIG. 6, 845

*Primary Examiner*—Linda J. Sholl
*Attorney, Agent, or Firm*—Morton J. Rosenberg; David I. Klein

[57] ABSTRACT

A drip syringe backpack frame is provided which includes an inverted T-shaped backpack plate adapted for releasable coupling to a user by means of a waist belt and a pair of shoulder straps. The inverted T-shaped backpack plate includes a pair of anchor sleeves disposed in longitudinally spaced relationship for securing an extendable drip syringe suspension rod thereto. The extendable suspension rod is formed by a longitudinally extended tubular outer tube in which is telescopically received an inner rod. The distal end of the inner rod is adapted for supporting a drip syringe solution container.

1 Claim, 4 Drawing Sheets

DRIP SYRINGE NEW BACKPACK FRAME

BACKGROUND OF THE INVENTION

When conventional drip syringes are utilized for the treatment of patients, the solution injected is often contained in a bag or bottle directly hung on a drip syringe suspension rod at the side of the bed and no matter whether the patient is reclining, sitting or standing at the side of the bed, the aforesaid drip syringe bag or bottle is higher than the syringe section to ensure the safe and practical injection of the drip solution; however, when patients able to leave the bed and ambulate want to use the lavatory, make a telephone call or go for a stroll, under the condition that the drip injection of the solution by the syringe system cannot be interrupted, frequently the drip solution bag or bottle must be manually raised by a nurse or family member of the patient and, furthermore, be maintained in physical position at the side of the patient during movement, or be kept lifted in position by the hand of the patient, or when the drip syringe solution bag or bottle (A) is suspended, as indicated in FIG. 1, from a lowerable drip syringe suspension rod (10), or the patient himself again moves or the patient directly grasps the drip syringe rod at the side of the bed and, furthermore, by means of one hand and the arm, it is undeniable that the aforesaid means can be utilized to bring the drip syringe solution nearer to the patient, but the inventor clearly understands that the positioning of the drip syringe solution bag and bottle by the aforesaid nurse and family member of the patient does not take safety into consideration, and in actuality is undeniably more troublesome, inconvenient and expends manpower, especially when the patient wants to use the lavatory, which creates an inconvenience that is quite apparent, and when the patient wants the freedom to take a walk, a procedure which involves the physical strength (specifically the strength of the arms) of accompanying personnel to bear the load and other shortcomings; when the drip syringe solution bag or bottle is directly held up in position by one hand of the patient, during a temporary or short period of operation, the weight of the drip syringe solution is sustained by the uplifted arm, but if the operation lasts for a prolonged period, not only will the physical strength of the patient be subjected to the production of an extremely large load, especially if the lifting arm gives rise to incomplete lowering, resulting in the danger of preventing the drip syringe solution from being injected into the body and, of course, the troublesomeness, inconvenience and additional burden on the patient due to this procedure is quite evident; furthermore, the aforesaid bag or bottle (A) of the drip syringe is suspended from a lowerable drip syringe rod (10) that, furthermore, the patient moves himself, which in relation to the aforementioned shortcomings of the expended manpower, the troublesomeness, the inconvenience and the increased burden on the patient, definitely provides a degree of effective improvement, however, the greatest shortcoming is that when the floor surface is sectionally variegated (such as at the doorsill or steps of a lavatory) or uneven in grade, the aforesaid lowerable drip syringe rod (10) cannot be easily moved and, furthermore, presents the danger of falling over if caution is not exercised since the aforesaid drip syringe rod is grasped directly by hand in a procedure dependent on the arm, and although the aforementioned shortcomings of sectional variegation or unevenness of the floor surface may not be present, the aforesaid drip syringe rod ultimately lacks stability and a secure anchoring point and will, according to the manual grasp of the patient and the direction of movement, along with shifts in height, or changes in the tightness or looseness of the grasp, therefore, increases the occurrence of unintentional situations if the grasp of the hand is not completely released and the danger of the drip syringe suspension rod falling to the floor occurs (a type of situation that easily occurs when using the telephone or the toilet) and, of course, is a type of procedure that produces a major limitation in the hands of the patient and causes both hands the impossibility of convenience, which is applicable in a range of actual operations.

Therefore, in view of the aforementioned operational drawbacks, the inventor of the invention herein conducted extensive research accompanied by the application of the academic theory to finally develop the invention herein that provides improvements over the aforementioned shortcomings by effectively enable the patient to have ease, convenience, safety and saving of manpower in utilization.

The primary objective of the invention herein is to provide a kind of drip syringe new backpack frame for medical treatment applications, of which the lightweight backpack plate consists of shoulder straps and a waist belt in a coordinated configuration that is simply and firmly secured to the back of the patient by the patient himself, and an extendible drip syringe suspension rod that is installed on the backpack plate and the drip syringe solution bag or bottle is directly suspended from the upper end of the drip syringe suspension rod, such that when the patient himself wants to partake in the aforesaid actions such as go to the lavatory or get up to take a stroll, make a telephone call and other activities, it is extremely convenient, simple and, furthermore, safe to do so, and can improve conventional methods that involve troublesomeness, inconvenience, waste of manpower and relatively unsafe procedures, wherein a nurse is required to lift the drip syringe solution bag, the patient must himself lift the syringe solution bag, the patient must additionally move the lowerable drip syringe suspension rod or the patient must additionally reposition the drip syringe suspension rod.

Another objective of the invention herein is to provide a kind of design that is extremely simple, installable, very easy to utilize and convenient that enables the patient to partake in the aforementioned activities such as going to the lavatory, making a telephone call, taking a walk and other sitting or standing actions, all of which can be easy, convenient and, furthermore, safer as it is completely self-operated and extremely suitable in actual utilization as well as ideal and progressive and, furthermore, the aforesaid drip syringe new type backpack frame for medical treatment has never been observed before.

To enable the examination committee to further understand and recognize the objectives, innovations and functions of the invention herein, the detailed description is accompanied by the brief descriptions of the drawings below:

DETAILED DESCRIPTION OF THE INVENTION

Figure 1:
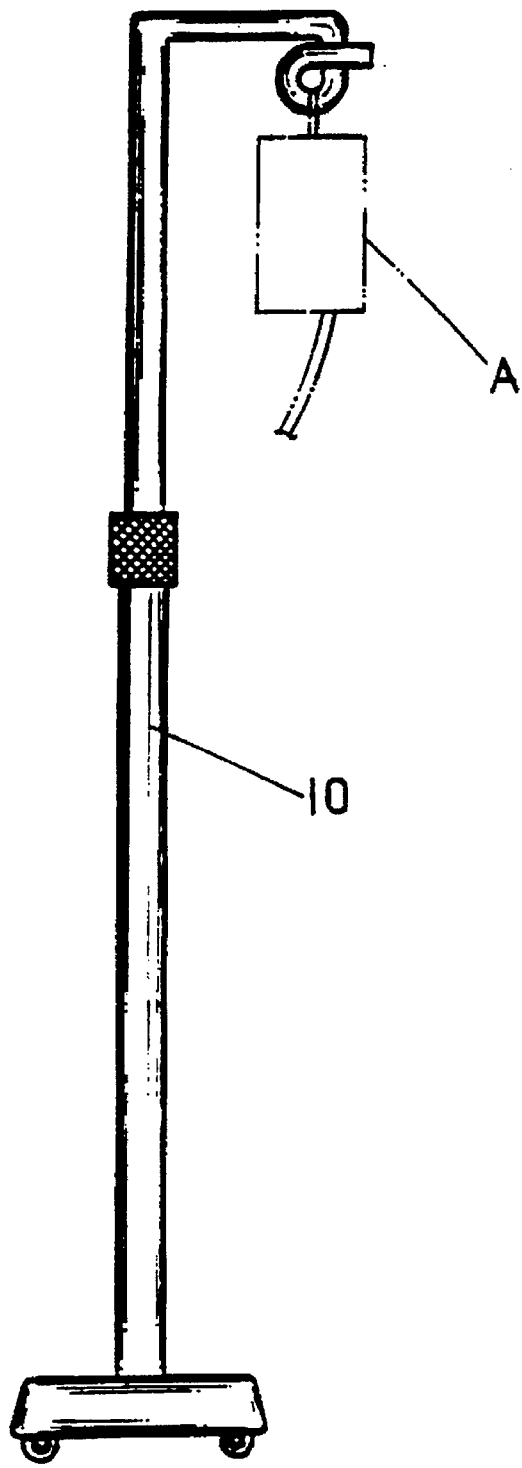
FIG. 1 is an orthographic drawing of a conventional lowerable drip syringe suspension rod.
Figure 2:
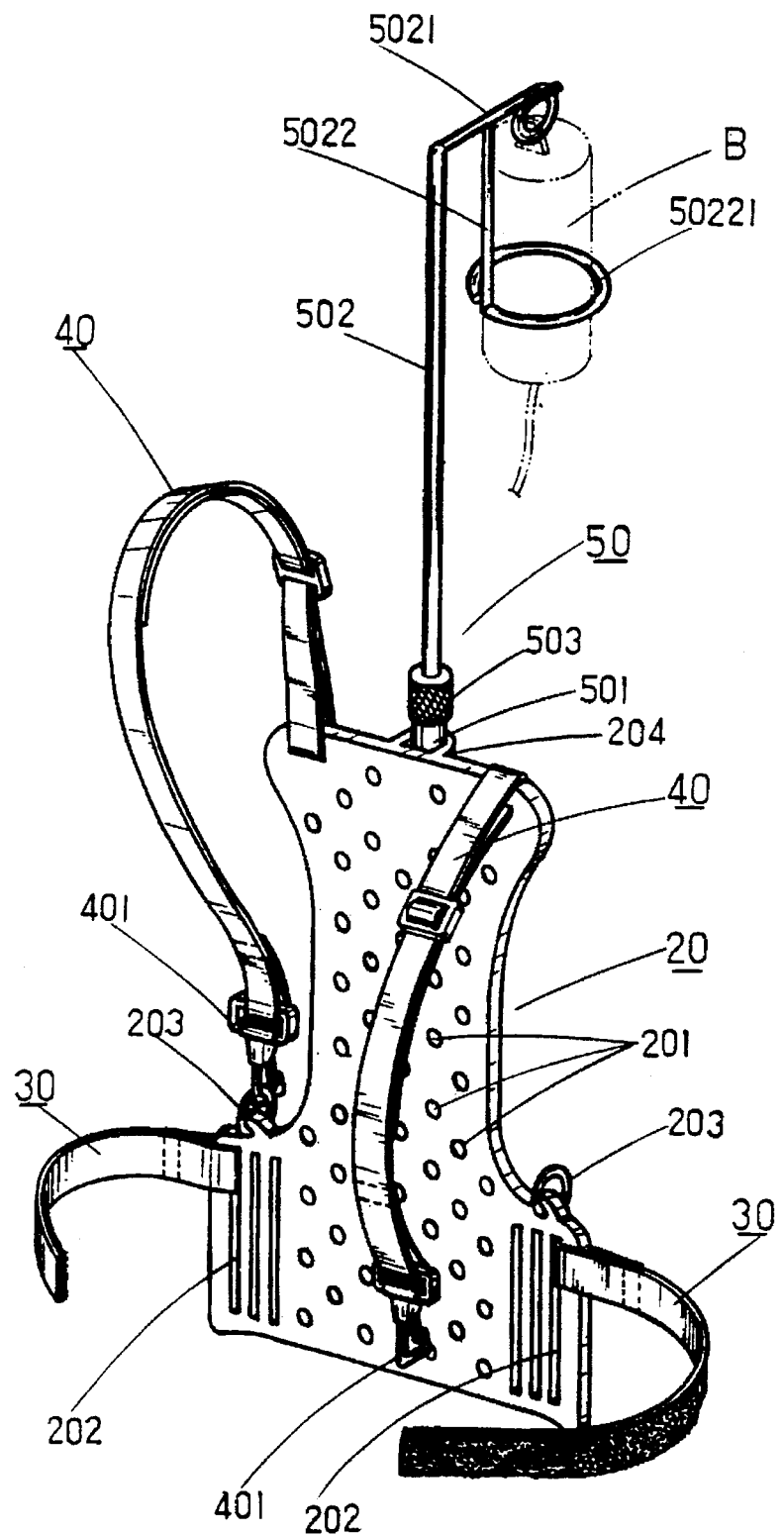
FIG. 2 is an isometric drawing of the invention herein.
Figure 3:
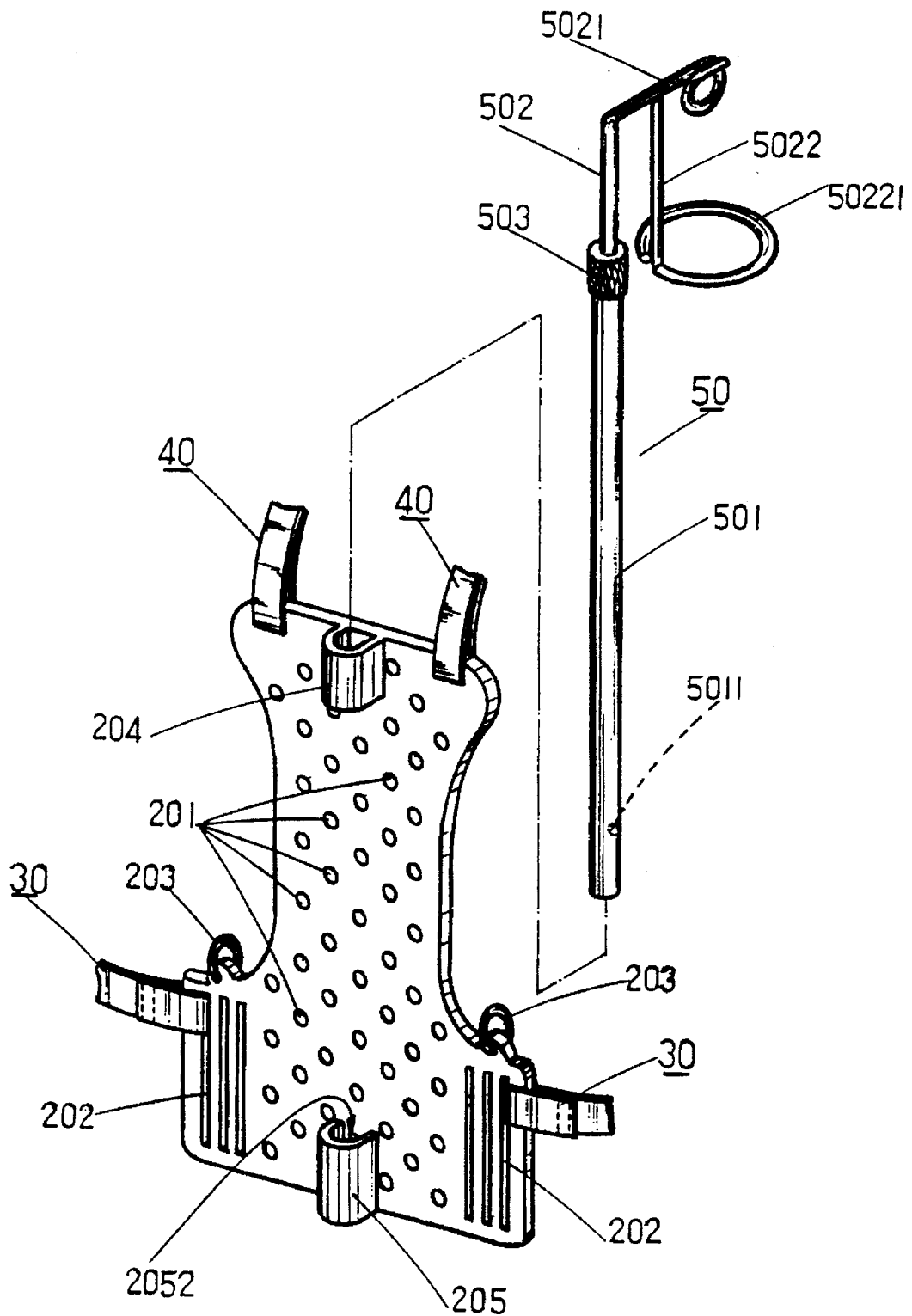
FIG. 3 is an isometric exploded drawing of the invention herein.
Figure 4:
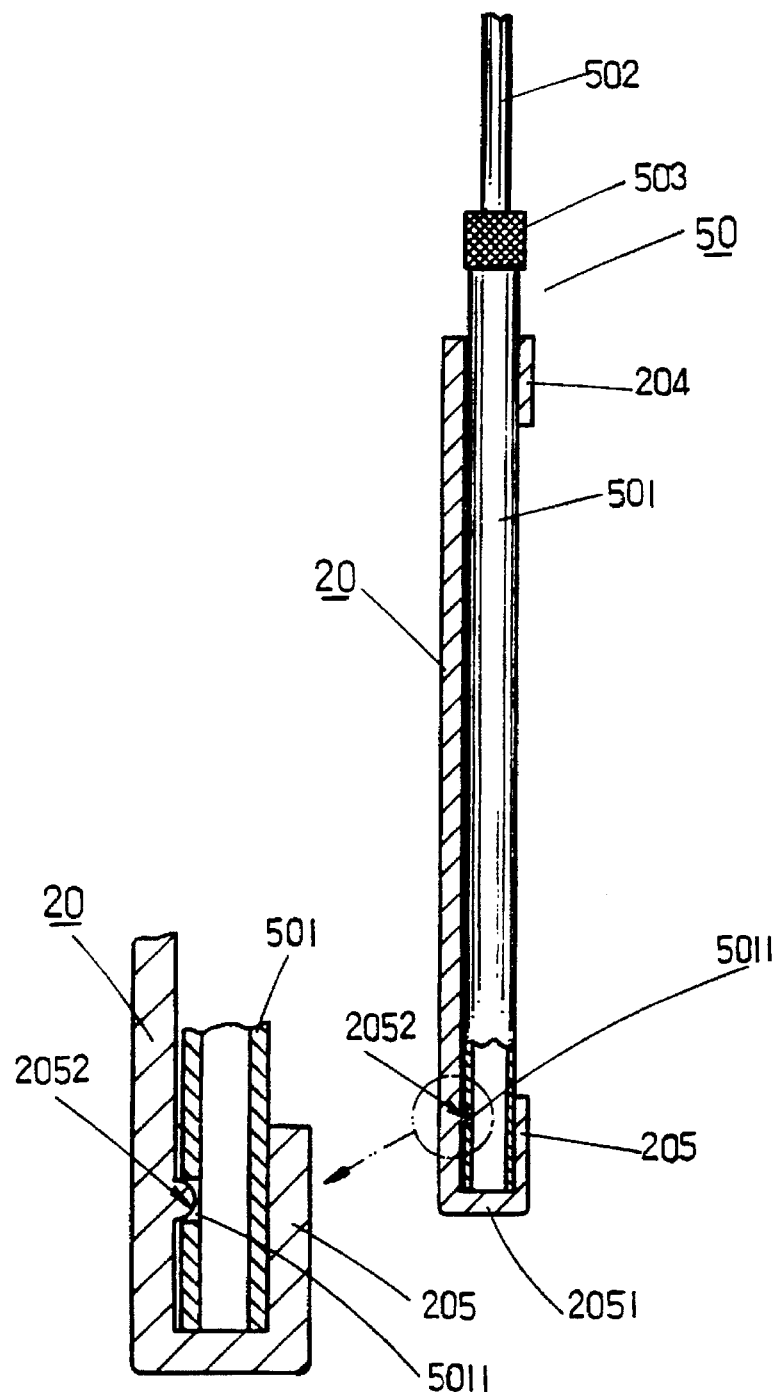
FIG. 4 is a cross-sectional drawing of the invention herein.

Referring to FIG. 2, FIG. 3 and FIG. 4, the invention herein is a drip syringe new backpack frame utilized in medical treatment that is mainly comprised of a backpack plate (20), a waist belt (30), shoulder straps (40) and an extendible drip syringe suspension rod (50); of which, the aforesaid backpack plate (20) consists of a lightweight and, furthermore, a material that is difficult to tear (such plastic or aluminum) formed in the general shape of an inverted T with a number of aeration holes (201) distributed throughout the surface, vertical slots (202) through the two lower sides, which in addition to serving as a means of ventilation also provides for the upward and downward adjustment of the inserted waist belt (30) and, furthermore, there is a fastening ring (203) suitably positioned at the lower extent of each of the two sides that provides for the attachment of the hook (401) at the end of the shoulder straps (40) installed at the upper extent of each of the two sides, and at the upper and lower ends at the center section of the rear surface are the upper and lower anchor sleeves (204) and (205) that are mounted along the same axis, and the aforesaid upper anchor sleeve (204) is entirely hollow and the lower anchor sleeve (205) has a tab plate (2051) at the lower end and, furthermore, a lip (2052) that is suitably positioned and projects at an appropriate height at the lower end; furthermore, the aforesaid drip syringe suspension rod (50) consists of two sections of lightweight, high durability aluminum material (aluminum alloy) that includes a extendible adjustment section, of which the aforesaid outer tube (501) is downwardly insertable into the upper and lower anchor sleeves (204) and (205) on the rear surface of the backpack plate (20) for positioning into the anchor hole (5011) at the lower end at same height as the anchor sleeve tab plate (2051) to the lip (2052) on the rear surface of the backpack plate (20) and thereby fastened to the protrusion of the lip (2052) on the backpack plate (20) that is enabled without turning or loosening, and the aforesaid can be shortened inwardly or extended outwardly in an operation wherein the inner rod (502), consisting of an upper end similar to a conventional horizontal suspension rod (5021) and the approximate center of aforesaid horizontal suspension rod (5021) consisting of a downward extending device having a suitable length and, furthermore, having a horizontal and appropriately large annular frame (50221) of the guard rod (5022), enabling after the bag or bottle (B) of the drip syringe solution is suspended at the horizontal rod suspension rod (5021) positioning inside the annular frame (50221), and not resulting in the occurrence of the hazard of swinging or falling and, of course, the operation of the aforesaid inner rod (502) extendible adjustment section and the fixed position outer rod (50), then consists of the same as that of a conventional drip syringe suspension rod, mainly consisting of an adjustment nut (503) that flexibly tightens against the inner section (not shown in the drawing) such that control over loosening or tightening is achieved and, therefore, is not further described in detail herein.

Based on the foregoing description of the structure of the invention herein, when operation for utilization is desired, the outer tube (501) of the aforesaid extendible-type drip syringe suspension rod (50) first consists of insertion into the upper and the lower anchor sleeves (204) and (205) on the rear surface of the backpack plate (20), and utilizing the upper end consisting of a lip (2052) protruding at a suitable height at the upper end of the aforesaid lower anchor sleeve (205), then the insertion of the aforesaid outer tube (501) naturally has an appropriate degree of positional tightness and, at the same time, due to the height of the anchor hole (5011) at the lower end of the aforesaid outer tube (501), then consisting of the similar position of the lip (2052) that protrudes from the rear surface of the backpack plate (20), therefore, an individual only has to slightly rotate the aforesaid outer tube (501) and of course, the anchor hole (5011) of the aforesaid outer tube (501) can be immediately and, furthermore, smoothly ensured to be clasped by the lip (2052) of the backpack plate (20), enabling the non-occurrence of any rotation or loosening phenomenon whatsoever; furthermore, when the aforesaid drip syringe solution and patients that cannot move themselves want to leave the bed to perform sitting or standing actions (for example, the aforementioned going to the lavatory, making a telephone call or taking a walk . . . etc., actions), it consists of first pulling the inner rod (502) of the aforesaid extendible drip syringe suspension rod (50) out to a certain length and then continuing by positioning on the rear section of the backpack plate (20) and, furthermore, the shoulder straps (40) and the waist belt (30) are adjusted to a suitable degree of tightness as directly fastened to the arms and the waist to enable the back placement on the drip syringe rod (50) of the backpack plate (20) and, furthermore, the aforesaid bag or bottle (B) originally suspended on the drip syringe suspension rod at the side of the bed at this time can be directly moved and suspended from the horizontal suspension rod (5021) of the extendible-type drip syringe suspension rod (50) on the rear section, and allowing the bag or bottle (B) to be directly positioned within the annular frame (50221) of the guard rod (5022) and, as such, the height of the drip syringe solution bag or bottle (B) after being suspended into position is necessarily higher than the head of the carrier and the position of the syringe injection section (generally in the proximity of the wrist), and under the conditions of completely not affecting the drip operation, of course, the immobilized patient can directly perform a range of sitting or standing actions easily, conveniently and, furthermore, safely and, furthermore, without affecting the normal actions of the two hands.

Furthermore, since in the foregoing description, the aforesaid backpack plate (20) and the extendible-type drip syringe suspension rod (50) are constructed of lightweight materials, therefore, after the drip syringe solution is placed on the back, an extremely small load will certainly be produced on the immobile patient and, furthermore, consist of being far lower than the aforementioned conventional method and at the same time, there are number of aeration holes (201) distributed throughout the surface of the backpack plate (20), thereby providing the back of the wearer a comfortable feeling by dissipating heat; furthermore, the aforesaid backpack plate (20) in addition to positioning achieved by adjusting the length of the shoulder straps (40), especially since the aforesaid waist belt (30) can be moved upward and downward in the long slots (202) on the two sides of the backpack plate (20), then with regard to the operation by users of various physical constitutions, still has directly provided effective operating convenience, comfort and secureness and, of course, the aforesaid waist belt (30) mutual coupling method, furthermore, has no special limitations, and it is only necessary to be a fixture having effective operating simplicity, convenience and secureness, for example, such as fastening by Velcro straps or male-female connector quick buckling, etc., methods that can be directly utilized.

Furthermore, the installation and utilization of the invention herein, in addition to the aforementioned that consisted of simplicity and convenience and can result in the movement of the patient being free, convenient and safe that is ensured to be more ideal, progressive and practical than conventional methods, it is worthy to indicate that since after the bag or bottle (B) of the drip syringe solution is suspended from the upper end of the drip syringe suspension rod (50), the movement of the bag or bottle is limited by the guard rod (5022) of the annular frame (50221) and falling off is circumvented by preventing large degrees of swing, and the outer tube (501) of the aforesaid drip syringe suspension rod (50) is clasped by the lip (2052) on the backpack plate (20) and the production of all rotation and loosening whatsoever is prevented, therefore, when the patient carrying the drip syringe solution moves, since the drip syringe solution is positioned securely, the effect is that the aforesaid is extremely well positioned and causes the person outfitted to feel extremely safe.

What is claimed is:

1. A drip syringe backpack frame, comprising:

an inverted T-shaped backpack plate having a plurality of aeration holes formed therethrough, said backpack plate having a central portion extending longitudinally between upper and lower ends thereof and a pair of opposing side portions extending transversely from said lower end of said central portion, each of said pair of side portions having a plurality of longitudinally elongated slots formed therethrough and a pair of fastening rings respectively secured thereto adjacent an upper edges thereof, said central portion having a rear surface with a pair of longitudinally spaced anchor sleeves coupled thereto, a first of said pair of anchor sleeves having a longitudinally directed first bore extending between opposing open ends thereof and a second of said pair of anchor sleeves having a second bore extending from an upper end thereof to a closed lower end and a tab extending into said second bore;

an extendable drip syringe suspension rod coupled to said backpack plate, said suspension rod having a longitudinally extended tubular outer tube received within said first and second bores of said first and second anchor sleeves and an inner rod telescopically received within said outer tube, said outer tube having through hole formed therein adjacent one end thereof for receiving said tab therein, said inner rod having a distal end adapted for supporting a drip syringe solution container;

waist belt means coupled on opposing ends to a respective one of said longitudinally elongated slots of each of said side portions for releasable securement around a user's waist; and, a pair of shoulder straps, each of said pair of shoulder straps being coupled to said upper end of said central portion on a first end thereof and releasably coupled to a respective one of said pair of fastening rings on an opposing second end thereof.

* * * * *